United States Patent [19]

Soodak

[11] Patent Number: 5,253,754
[45] Date of Patent: Oct. 19, 1993

[54] PEEL PACKAGE AND METHOD OF PACKAGING ORGANS

[75] Inventor: Charles I. Soodak, Silver Spring, Md.

[73] Assignee: American Fluoroseal Corporation, Silver Spring, Md.

[21] Appl. No.: 929,205

[22] Filed: Aug. 14, 1992

[51] Int. Cl.[5] ............................................. B65D 81/18
[52] U.S. Cl. .................................... 206/438; 53/455; 206/484; 383/210; 493/189
[58] Field of Search ............... 53/425, 428, 455; 206/205, 210, 213.1, 363, 364, 438, 439, 440, 63.3, 484, 484.1; 383/94, 210, 211; 493/189

[56] References Cited

U.S. PATENT DOCUMENTS

| | | |
|---|---|---|
| 3,123,210 | 3/1964 | Hermanson et al. . |
| 3,425,865 | 2/1969 | Shelton, Jr. . |
| 3,754,700 | 8/1973 | Bank . |
| 3,761,013 | 9/1973 | Schuster . |
| 3,768,725 | 10/1973 | Pilaro . |
| 3,926,311 | 12/1975 | Laske . |
| 3,938,659 | 2/1976 | Wardwell . |
| 3,942,529 | 3/1976 | Waage . |
| 3,991,881 | 11/1976 | Augurt . |
| 3,995,739 | 12/1976 | Tasch et al. . |
| 4,022,256 | 5/1977 | Berkman et al. . |
| 4,121,714 | 10/1978 | Daly et al. . |
| 4,145,001 | 3/1979 | Weyenberg et al. . |
| 4,146,133 | 3/1979 | Bogorad et al. . |
| 4,168,779 | 9/1979 | Yokokoji et al. . |
| 4,190,154 | 2/1980 | Clark . |
| 4,206,844 | 6/1980 | Thukamoto et al. . |
| 4,296,179 | 10/1981 | Wardwell . |
| 4,306,656 | 12/1981 | Dahlem . |
| 4,352,429 | 10/1982 | Newman . |
| 4,358,015 | 11/1982 | Hirsch . |
| 4,407,874 | 10/1983 | Gehrke . |
| 4,468,811 | 8/1984 | Shaw et al. . |
| 4,539,793 | 9/1985 | Malek . |
| 4,644,586 | 2/1987 | Padgett . |
| 4,660,721 | 4/1987 | Mykleby . |
| 4,781,297 | 11/1988 | Abrahamsson et al. . |
| 4,874,090 | 10/1989 | Dyke . |
| 4,945,203 | 7/1990 | Soodak et al. . |
| 4,951,815 | 8/1990 | Ulbrich . |
| 5,031,762 | 7/1991 | Heacox ............................. 206/210 |

Primary Examiner—Jimmy G. Foster
Attorney, Agent, or Firm—Roylance, Abrams, Berdo & Goodman

[57] ABSTRACT

A package for transporting an organ is formed from a plastic laminate. The laminate includes an inner layer of a fluorinated polyethylenepropylene copolymer and an outer layer of a polyimide. The laminates are heat sealed together around the perimeter to form a closed pouch. The thickness of the inner and outer layers of the laminate and the bond strength between the layers of the laminate are tailored to produce a peelable seal. Upon peeling the laminated sheets apart, the heat seal will tear along the edge of the seal and the inner layer will delaminate from the outer layer.

22 Claims, 3 Drawing Sheets

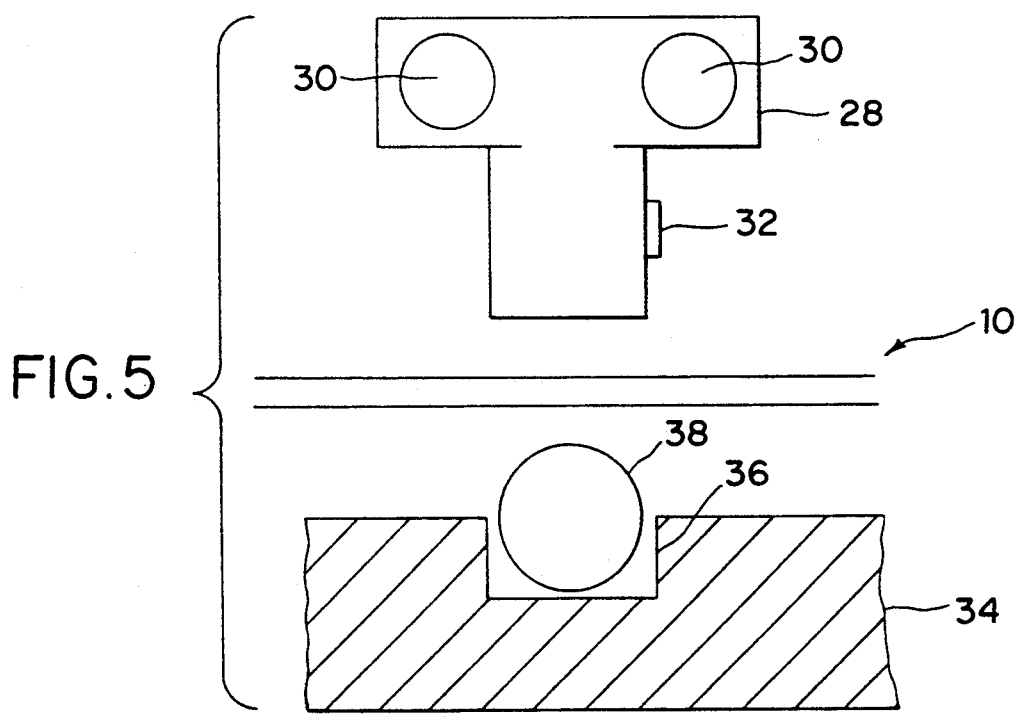

PEEL PACKAGE AND METHOD OF PACKAGING ORGANS

FIELD OF THE INVENTION

The present invention relates to peel pouches as used in the packaging of medical devices, equipment, and transplant organs. More particular, the invention relates to a peel pouch which can be subject to liquid nitrogen temperatures without becoming brittle. The invention further relates to a heat sealer to be used with this material.

BACKGROUND OF THE INVENTION

Packages and particularly pouches having a peelable seal are well known in the medical field for containing sterile equipment. A peel pouch is an envelope or pouch often times constructed by welding two films together around three sides leaving one end open. An object is then placed inside the pouch, and the pouch then sealed on the fourth side. The pouch usually has an end with generous flaps which may be held in the hands and pulled apart. When this is done, the pouch peels open, revealing its contents in a manner such that they may be removed without any additional contact with the exterior surfaces of the pouch. This peel characteristic is accomplished by using a special adhesive to bond the films together, such that the adhesive strength is lower than the tear strength of the films.

In the medical and biotechnology fields, there are many uses for peel pouches. When an operator opens the pouch by peeling the layers apart, the contents of the pouch can be withdrawn from the pouch without violating sterility. In contrast, a simple bag must be cut open with a scissors or knife which can carry contamination into the interior of the bag or damage the contents.

The peeling process is typically facilitated by the use of a chevron shaped seal at one end. The seal is formed by heat sealing in the shape of a "v" whose apex points outward from the interior of the pouch. Peel tabs formed from excess lengths of the back and the front films extend outward from the pouch past the chevron seal. When the operator pulls on the peel tabs, the tearing of the adhesive is started by the apex of the chevron. In addition to the use of a chevron and peel tabs, the adhesive seal must have a peel strength below the tensile strength of the films which comprise the front and back of the pouch, so that during peeling the adhesive fails but the films do not tear.

Many peel pouches consist of a clear film on one side and a paper layer on the other side. This allows visual examination of the contents while they are still in the pouch, while the paper allows penetration of gas or steam for the sterilization of the contents. The clear film is usually a dual layer film such as polyester bonded to polypropylene. The polypropylene serves as a hot melt adhesive which allows the film to be bonded to the paper backing. Upon peeling, the polypropylene delaminates a thin layer from the surface of the paper, allowing a controlled strength peel.

In the organ transplantation field, an outer pouch frequently consists of a metal foil-polyethylene laminate. This laminate has the disadvantages in that it is not transparent and occasionally breaks during shipping at liquid nitrogen temperatures. In addition, the pouch is not peelable, and so has to be cut open with sterile scissors at the time of use. This creates the risk of contamination entering the interior of the pouch bag. The inner pouch is a nylon polyethylene laminate which is transparent, but is subject to embrittlement when frozen at liquid nitrogen temperatures.

Peel pouches heretofore have had the disadvantage of being produced from materials which are not stable at cryogenic temperatures and become extremely brittle at such storage temperatures. These pouches are therefore unsuitable for storing materials, such as biological tissue and cells, at cryogenic temperatures. Examples of this type of peel pouch are found in U.S. Pat. No. 4,358,015, U.S. Pat. No. 4,352,429, U.S. Pat. No. 4,190,154 and U.S. Pat. No. 4,121,714.

Packages are also known which can be used to store blood or other materials at cryogenic temperatures. These packages do not include peelable seals, thereby requiring the package to be cut by scissors or a knife, and risking contamination of the contents. An example of this type of package is disclosed in U.S. Pat. No. 3,942,529.

SUMMARY OF THE INVENTION

The package produced in accordance with the invention obviates the disadvantages and limitations of the previous packages while providing an effective package which can maintain the contents in a sterile condition. The present invention is directed to a package which can be easily heat sealed and provided with a peelable seal to reduce the risk of contamination of the sterile interior of the package.

It is therefore an object of the invention to produce a package which can be easily opened without the need for scissors, a knife or other tool to contaminate the package or its contents.

It is a further object of the invention to produce a sterile package which remains flexible at cryogenic temperatures.

Another object of the invention is to produce a package that is sufficiently transparent to enable viewing of the contents at cryogenic temperatures.

Another object of the present invention is to provide a new and improved method and apparatus for the manufacture of a package, bag or the like for biomedical use fabricated from laminated films having thicknesses on the order of 0.5 to 2 mils and preferably about 1 mil in which the welds are of maximum strength and the edges of the finished articles are smooth and free of burrs.

A further object of the invention is to provide a new and improved process and apparatus for manufacturing animal organ bags in which the bags can be large and strong, yet dies are not required for their manufacture, and the process is simple and economical.

The above objects of the invention are basically attained by producing a peelable package comprising a first laminate layer including an inner layer of fluorinated ethylene propylene copolymer and an outer layer of a nonthermoplastic polyimide; a second laminate layer heat welded to said first layer to define a continuous peelable seal and closed inner cavity, the second laminate layer including an inner layer of a fluorinated ethylenepropylene copolymer and an outer layer of a nonthermoplastic polyimide having a melting temperature higher than said inner layer; the inner layer of the first laminate layer being heat sealed to the inner layer of the second layer to define said peelable seal; the inner layers of the first and second laminates each having a thickness such that the inner layers have a tear strength less than the bond strength between the inner and outer laminate layers.

Other objects of the invention are basically attained by a method of packaging a transplantable animal organ in a peelable package, the method comprising superimposing first and second laminate layers including an inner layer of fluorinated ethylene propylene copolymer and an outer layer of a nonthermoplastic polyimide, the first and second laminate layers being superimposed with the inner layers facing one another; heat sealing the first and second laminate layers together to form first and second spaced apart side seams and a first end seam extending between said side seams to form an open-ended cavity; placing a transplantable animal organ in the open-ended cavity; and heat sealing a second end seam extending between said side seams to define a closed cavity containing said organ; the inner layers of the first and second laminate layers having a thickness such that the inner layers have a tear strength less than the bond strength between the inner and outer laminate layers.

BRIEF DESCRIPTION OF THE DRAWINGS

The advantages and description of the invention are discussed in conjunction with the drawings also forming a part of this disclosure, and in which:

FIG. 5 is a side view of the heat sealing apparatus in accordance with the invention.

DETAILED DESCRIPTION OF THE INVENTION

The present invention is directed to a pouch or package having a peelable seal and to a method of producing the pouch. The invention is further directed to a method of storing an organ for transplantation using the novel pouch of the invention.

In the field of organ transplants the packages and pouches used in transporting the organ must satisfy several requirements. The pouches for use in organ transplantation must maintain sterile conditions, be able to transport the organ safely at liquid nitrogen temperatures, and be opened easily at the site without contaminated instruments contacting the organ.

The pouch should be sufficiently transparent to allow examination of the organ prior to opening the pouch. The organs are usually double sealed in a first bag within a second bag and frozen in liquid nitrogen. The organ may be sealed while immersed in a cryoprotectant (freezing fluid) which typically contains DMSO, a very aggressive chemical. The inner surface of the pouch must be noncontaminating, inert, and harmless to living human cells. The bag further must be able to withstand the low temperatures at liquid nitrogen temperatures without becoming brittle or weak.

The pouch must arrive clean at the organ bank where the organs are inserted into the pouch. The pouch must also be resistant to the rigors of sterilization without losing its physical or chemical properties or absorbing the sterilizing gas. An opening for the organ must be provided, or an easy and sterile means for opening the pouch must be provided. The opening must be sealable under sterile conditions at the transplant center by use of reasonably simple machinery and procedures. The outer surface of the pouch must be able to accept ink for labeling and for writing on the pouch at the time of organ insertion.

The pouch and method of packaging organs in accordance with the invention satisfies all of the requirements for transporting organs. The pouch is transparent to allow inspection of the organ before opening, easily sterilized without destroying the properties of the pouch, and able to withstand storage at temperatures of liquid nitrogen.

Figure 1:
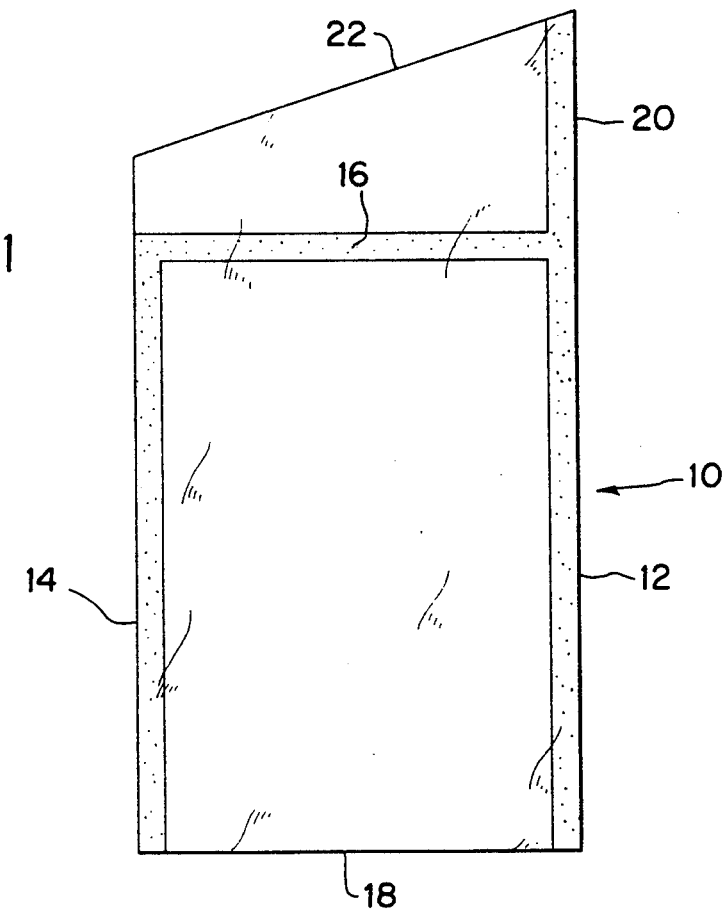
FIG. 1 is top plan view of a first embodiment of the pouch in accordance with the invention.

Referring to FIG. 1, the pouch 10 for storing and transporting animal organs and in particular human organs is formed from a two-layer laminate. Two sheets of the laminate are placed together and heat sealed along the edges to form side seams 12, 14 and along at least one end to form an end seam 16. As shown in FIG. 1, the pouch is initially formed with an open end 18.

In preferred embodiments, one of the side seams 12 extends beyond the end seam 16 to form a leg 20 and triangular shaped tabs 22. The tabs 22 enable the user to easily grip each of the sheets and pull the sheets apart to open the pouch as discussed hereinafter in greater detail.

The laminate which is used to form the pouch includes an inner layer of a material which is chemically inert to the organ. A material that is particularly desirable is a fluorinated ethylenepropylene copolymer, such as tetrafluoethylene-hexafluoropropylene copolymer. A suitable material for use in producing the pouch is produced by E.I. DuPont under the tradename Teflon-FEP. This inner layer of the fluorinated ethylenepropylene copolymer has a relatively low strength and must be reinforced by an outer layer of durable material to resist wear and rupture during use. A particularly suitable material for the outer wear layer is a non-thermoplastic polyimide such as that produced by E.I. DuPont and sold under the name Kapton. The material is sold as a laminate having a layer of fluorinated ethylenepropylene copolymer bonded to a layer of a polyimide. One such laminate is sold under the name Kapton-Type H by Dupont. Similar laminates are also available from Daikin of Japan and Hoechst AG of Germany.

In alternative embodiments, the laminate may have a greater number of layers. The inner layer should, however, be a fluorinated ethylene propylene copolymer.

The above described laminate is particularly desirable for producing pouches for transporting and packaging organs since the material is able to withstand freezing at the low temperatures of liquid nitrogen. In addition, the laminate is able to withstand sterilization temperatures by heating to as high as 200° C. The laminate and the resulting pouch may be used in a very broad temperature range from freezing at cryogenic temperatures to sterilizing temperatures.

The outer layer of the laminate preferably has a melting point higher than the inner. In preferred embodiments, the outer layer is able to withstand temperatures up to about 400° C. without delaminating from the inner layer. The inner layer preferably has a melting point range of about 300° C. such that the inner layer can be heat welded to the inner layer of an adjacent film.

The laminate of a polyimide and fluorinated ethylene-propylene copolymer provide a heat sealable pouch that is impervious to dimethylsulfoxide (DMSO) and is compatible with living cells. The outer polyimide layer is sufficiently strong to provide a wear resistant layer and to provide sufficient strength for peeling the package open.

In embodiments of the invention, the layers of the laminate are relatively thin, generally in the range of 0.5 to 2 mils (12 to 50 microns) each, preferably about 0.5 to 1 mil each. In a preferred embodiment of the invention, each layer of the laminate is about 1 mil each. The use of thin films reduces the strain on the package when frozen, and thus, reduces the tendency to crack when frozen. Thin layers further provide for the necessary transparency of the pouch. The polyimide has a natural brown color which can make the pouch opaque if the film is too thick.

The thickness of the films is important in providing the peel characteristics of the finished pouch. The films must be sufficiently thick to provide the required strength to the pouch. The inner layer of fluorinated ethylenepropylene copolymer must be sufficiently thin so that the inner layer easily tears from the laminate during opening. Conversely, the outer polyimide layer must be sufficiently thick to provide the strength to ensure the outer layer will not tear during opening.

In preferred embodiments, the inner and outer layers are substantially the same thickness. In alternative embodiments the films may be of different thicknesses provided the inner layer is su thin to tear during opening. In preferred embodiments, the thickness of the outer polyimide film is equal to or greater than the thickness of the inner layers.

Also important to the strength of the pouch and the peel characteristics of the seal is the bond strength between the layers of the laminate. The bond strength between the layers of the laminate is selected so that when the two sheets of laminate are peeled apart, one only if the inner layers, along the seam delaminates from the outer layer and tears along the seam. If the bond strength between the layers of the laminate is too weak, the entire outer layer will delaminate leaving behind a skin of the inner layer on the opposing laminate thereby leaving the organ enclosed in the pouch. A bond between the inner and outer layers which is too strong will not delaminate easily during opening thus forcing the laminate or the welded seal to tear when opening the pouch.

The bond strength between the inner fluorinated ethylene propylene copolymer and the outer polyimide layer may be controlled by various treatments during the manufacturing of the laminate. For example, the polyimide layer may be subjected to a corona discharge treatment before laminating to the fluorinated ethylenepropylene copolymer. Alternatively, the laminate may be baked after the fluorinated ethylenepropylene copolymer is laminated to the polyimide to enhance adhesion.

The fluorinated ethylenepropylene copolymer film in preferred embodiments is subjected to corona discharge treatment only on the side adjacent the polyimide layer to maintain sterility of the side forming the inner surface of the pouch. In many laminates, the manufacturer subjects the fluorinated ethylenepropylene film to a corona discharge treatment on both sides. It is important to maintain the surfaces of the laminates contacting the organ in as pure a state as possible.

The pouch 10 is produced by overlaying two sheets of the laminate in physical contact with the fluorinated ethylenepropylene layers contacting each other. The laminates are pressed between a heated bar to apply heat through the outer layers to melt the inner layers without melting the outer layers. The heat is applied for a sufficient length of time to completely fuse the inner layers together and form seals 12, 14 and 16. As shown in FIG. 1, a side seam 20 is formed which extends from the body of the pouch. A substantially triangular shaped flap 22 of the laminates extends from the seals 16 and 20.

Figure 2:
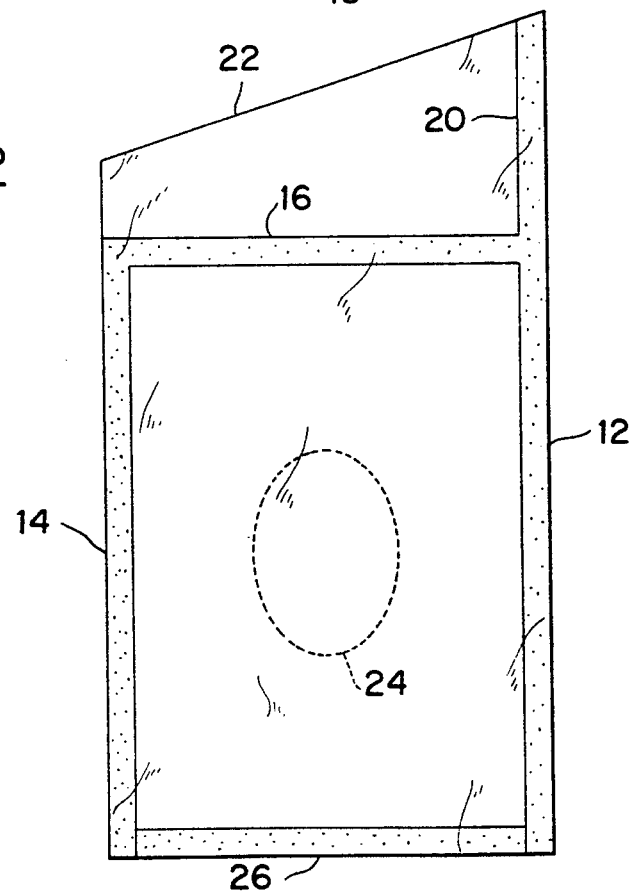
FIG. 2 is top plan view of the pouch of FIG. 1 containing an animal organ and being heat sealed.

In use, an organ 24 shown in phantom lines in FIG. 2 is inserted through the open end 18 of the pouch 10. A bottom seal 26 is formed by applying heat to fuse the inner layers together. The pouch may then be frozen and shipped to the desired destination.

Prior to use, the pouch is sterilized by conventional practices. In addition, suitable indicia or a logo may be applied to the outer surface by conventional silk screening techniques.

The sealing device in a preferred embodiment is illustrated in FIG. 5. The device includes a temperature controlled bar 28. Heating elements 30 are provided in the bar to heat the device. A thermocouple 32 is used to maintain the desired temperature. The bar 28 is mounted for reciprocating motion to press the sheets of pouch 10 between the bar 28 and a platen 34. The platen 34 includes a groove 36. A silicone rubber cord 38 is positioned in the groove 36 to press the sheets of the laminate against the bar 28.

Chevron peel seals as are known in the art have been found difficult to make using the laminated sheets. Thus, one end of the pouch is extended as shown in FIG. 1. The end is trimmed to leave a sharp pointed corner. The pointed corner will start a tear in the inner layer of the laminate and propagate along the seam as the sheets are pulled apart. In alternative embodiments, the pouch may include a chevron shaped seal.

Figure 3:
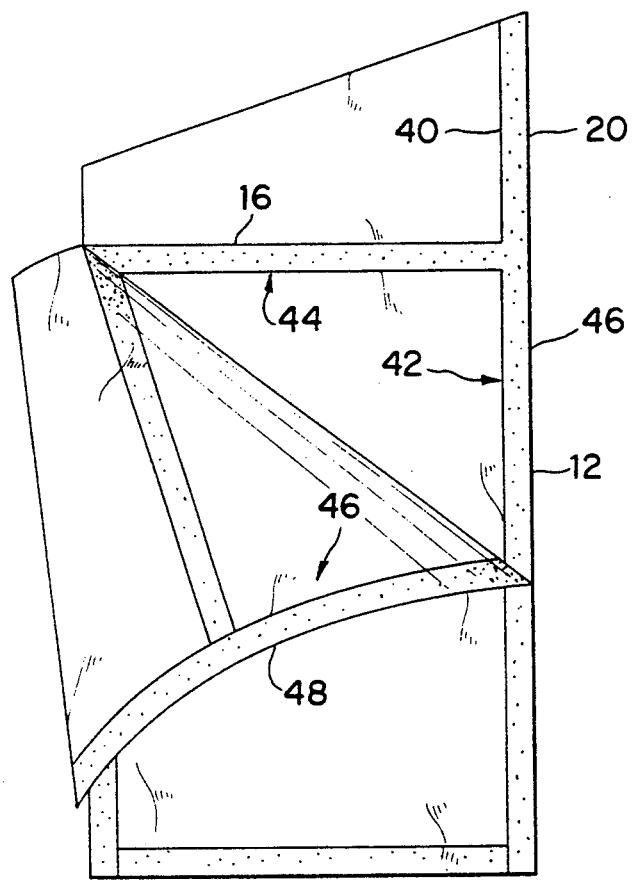
FIG. 3 is perspective view of the pouch of FIG. 2 in the partially open state.

During opening of the pouch 10 as shown in FIG. 3, the seal 20 will start to tear along the inner edge 40 and propagate to the inner edge 42 of side seal 12 and the inner edge 44 of the end seal 16. Also, the inner layer 46 of the laminate and the welded seal 48 of the fluorinated copolymer layer between the laminates separates from the outer layer to expose the polyimide layer 46.

Figure 4:
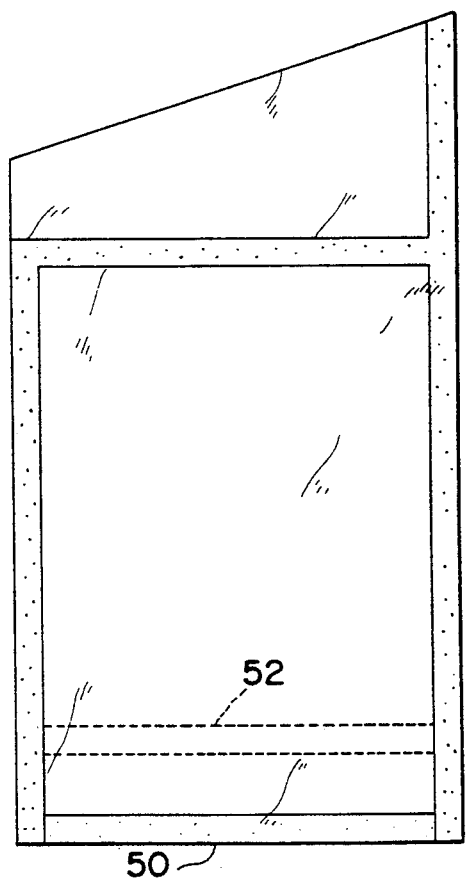
FIG. 4 is a top plan view of a second embodiment of the pouch of the invention.

In an alternative preferred embodiment, the pouch is produced having four sealed edges as illustrated in FIG. 4. The completely sealed pouch is thus easily maintained in a sterile condition. Subsequent handling of the pouch, such as for silk screening, will not contaminate the interior of the pouch. The pouch thus arrives at the site in a completely sterile condition.

In use, the operator cuts one of the end seals from the pouch, such as end seal 50 as shown in FIG. 4, to produce an open ended pouch similar to that illustrated in FIG. 1. The pouch may then be sterilized as needed before the organ to be transported is placed in the pouch. A second end seam 52 as shown in phantom lines of FIG. 4 is then formed by heating the laminates as before between the platen and the heated bar. The pouch is completely sealed to enclose the organ so that the pouch can be labeled and shipped. The sealed pouch is t frozen under liquid nitrogen and transported to the desired destination. The pouch is then opened by peeling the sheets apart so the organ can be removed.

In a further embodiment, the pouch is produced by sealing all of the edges as discussed above to form a closed pouch. When the pouch is ready for use, one of the end seals is peeled open instead of being cut. By peeling the pouch open, the risk of contamination of the interior of the pouch is reduced. The organ is then placed in the pouch and a new heat seal is formed as above to again close the pouch. The pouch is then frozen and transported.

The pouch is able to receive the organ without any additional preparation. In practice, however, the organ is generally packaged with a cryoprotectant, which often contains DMSO. The organ may further be placed in an inner pouch or package before packaging in the peelable pouch of the invention, if desired.

The above description is intended to be exemplary of embodiments of the invention. It is to be understood that numerous alternative embodiments and variations can be made without departing from spirit and scope of the invention.

What is claimed is:

1. A cryogenic temperature stable peelable package for storing and transporting transplantable organs at cryogenic temperatures comprising:
   a first laminate including an inner layer of fluorinated ethylenepropylene copolymer and an outer layer of a nonthermoplastic polyimide;
   a second laminate heat welded to said first layer to define a continuous peelable seal and a closed inner cavity, said second laminate including an inner layer of a fluorinated ethylenepropylene copolymer and an outer layer of a nonthermoplastic polyimide, said polyimide having a melting temperature higher than said inner layer;
   said inner layer of said first laminate being heat sealed to said inner layer of said second laminate to define said peelable seal;
   said inner layer of said first and second laminates having a thickness such that said inner layers have a tear strength less than the tear strength of said outer layers and said inner and outer layers having a bond strength such that said inner layer delaminates from said outer layer upon peeling said peelable seals open substantially without tearing said outer layer.

2. The peelable package according to claim 1, said second layer having a thickness of about 0.5 to 2 mils.

3. The peelable package according to claim 1, said first layer having a thickness of about 0.5 to 2 mils.

4. The peelable package according to claim 1, wherein said heat seal between said first and second laminates has a bond strength greater than a bond strength between said inner and outer layers of said laminates.

5. The peelable package according to claim 1,
   said package having first and second spaced-apart side seams;
   first and second spaced apart end seams extending between said side seams to define a package cavity;
   at least one of said end seams being spaced from an end of at least one of said side seams.

6. The peelable package according to claim 1, further comprising a transplantable animal organ contained within said package.

7. The peelable package according to claim 1, said first and second laminates being about 0.5 to 1 mil.

8. The peelable package according to claim 1, each of said first and second laminates being about 1 mil.

9. A method of producing a cryogenic temperature stable, peelable package for storing and transporting transplantable organs at cryogenic temperatures comprising:
   superimposing first and second laminates, said laminates including an inner layer of fluorinated ethylenepropylene copolymer and an outer layer of a nonthermoplastic polyimide, said first and second laminates being superimposed with the inner layers facing one another;
   heat welding said first and second laminates together to form first and second spaced apart side seams and first and second end seams to define a continuous peelable seem forming a closed cavity;
   said inner layers of said first and second laminates having a thickness such that said inner layers have a tear strength less than a tear strength of said outer layers, and said inner and outer layers having a bond strength such that said inner layer delaminates from said outer layer substantially without tearing said outer layer upon peeling said peelable seals open.

10. A method according to claim 9, each of said first and second layers of said laminates having a thickness of about 0.5 to 2 mils.

11. The method according to claim 9, each of said first and second layers of said laminates having a thickness of about 1 mil.

12. The method according to claim 9, comprising heat welding said first and second laminates such that said peelable seal has a bond strength greater than a bond strength between said inner and outer layers of said laminates whereby said inner layer delaminates from said outer layer upon peeling said peelable seal open.

13. A method of packaging a transplantable animal organ in a cryogenic temperature stable peelable package, said method comprising:
   superimposing first and second laminates including an inner layer of fluorinated ethylenepropylene copolymer and an outer layer of a nonthermoplastic polyimide, said first and second layers being superimposed with the inner layers facing one another;
   heat sealing said first and second laminates together to form first and second spaced-apart side seams and a first end seam extending between said side seams to form an open-ended cavity;
   placing a transplantable animal organ in said open-ended cavity; and
   heat sealing a second end seam extending between said first and second side seams to define a peelable seal and a closed cavity containing said organ;
   said inner layers of said first and second layers of said laminate having a thickness such that said inner layers have a tear strength less than a tear strength of said outer layers, and said inner and outer layers having a bond strength between one another such that said inner layer delaminates from said outer layer substantially without tearing said outer layer upon peeling said peelable seal open.

14. The method according to claim 13, further comprising
   heat sealing a second end seam extending between said side seams before placing said organ in said cavity to define a closed package;
   opening said package along at least one of said end seams to form an open-ended cavity;
   thereafter placing said organ in said cavity; and
   heat sealing said package along said open end to form a third end seam and to enclose said organ.

15. The method according to claim 14, wherein said step of opening said package comprises peeling said at least one end seam to define said open-ended package; and heat sealing said open-ended package after placing said organ in said cavity along said open end to form a third end seam spaced from said second end seal and extending between said side seams.

16. The method according to claim 14, wherein said step of opening said package comprises cutting said package adjacent said at least one end seam to form an open-ended package, and heat sealing said open-ended package, after placing said organ in said package, to form a third end seam and to form a closed package.

17. The method according to claim 13, each layer of said first laminate having a thickness of about 0.5 to 2 mils.

18. The method according to claim 13, each layer of said second laminate having a thickness of about 0.5 to 2 mils.

19. The method according to claim 13, further comprising forming at least one of said end seams in a position spaced from at least one end of said laminates a distance to define a pair of pull strips.

20. The method according to claim 13, further comprising forming said first side seam a distance spaced from a first end of said first and second side seams to define a pair of pull strips.

21. The method according to claim 13, wherein said peelable seal between said inner layers of said first and second layers has a bond strength greater than a bond strength between said inner and outer layers of said laminates whereby said inner and outer layers delaminate upon peeling said seal open.

22. The method according to claim 13, said heat seals being formed by positioning said first and second layers between a platen comprising a silicone rubber cord, and a movable heated welding bar movable with respect to said platen; moving said welding bar toward said platen to compress said first and second layers between said heated welding bar and said silicone rubber cord to melt said inner layers together substantially without melting said second layer and to form said peelable seal.

* * * * *